(12) United States Patent
Lee et al.

(10) Patent No.: US 6,840,103 B2
(45) Date of Patent: Jan. 11, 2005

(54) ABSOLUTE HUMIDITY SENSOR

(75) Inventors: Don Hee Lee, Kyonggi-do (KR); Hyung Ki Hong, Kyonggi-do (KR)

(73) Assignee: LG Electronics Inc., Seoul (KR)

( * ) Notice: Subject to any disclaimer, the term of this patent is extended or adjusted under 35 U.S.C. 154(b) by 78 days.

(21) Appl. No.: 10/088,556

(22) PCT Filed: Dec. 12, 2000

(86) PCT No.: PCT/KR00/01439
§ 371 (c)(1),
(2), (4) Date: Mar. 19, 2002

(87) PCT Pub. No.: WO02/06808
PCT Pub. Date: Jan. 24, 2002

(65) Prior Publication Data
US 2002/0149486 A1 Oct. 17, 2002

(30) Foreign Application Priority Data

Jul. 19, 2000 (KR) .................................. 10-200-0041374

(51) Int. Cl.[7] .............................................. G01N 27/18
(52) U.S. Cl. .................. 73/335.05; 73/29.01; 73/29.05; 388/35; 361/286
(58) Field of Search ........................... 73/29.01, 29.05, 73/335.05; 338/35; 361/286; 340/602, 693.5, 693.6

(56) References Cited

U.S. PATENT DOCUMENTS 5,388,443 A * 2/1995 Manaka ..................... 73/29.05
5,551,283 A * 9/1996 Manaka et al. ............ 73/29.01
5,659,127 A * 8/1997 Shie et al. ................ 73/335.05

FOREIGN PATENT DOCUMENTS

| EP | 021225 A1 | 1/1981 | ............... 73/335.05 |
| EP | 0376721 A2 | 7/1990 | ................ 73/29.01 |
| GB | 2172999 | * 10/1986 | ................ 73/29.01 |

* cited by examiner

Primary Examiner—Daniel S. Larkin
(74) Attorney, Agent, or Firm—Birch, Stewart, Kolasch & Birch, LLP

(57) ABSTRACT

An absolute humidity sensor for a microwave oven is disclosed. The absolute humidity sensor includes a substrate having a first hole and a second hole in a predetermined region, a membrane formed on the substrate, a humidity sensing element formed on the membrane where the first hole is formed, for detecting humidity exposed to the air, having a variable resistance value depending on the detected humidity, and a temperature compensating element formed on the membrane where the second hole is formed, for compensating for the resistance value of the humidity sensing element. For package, the absolute humidity sensor further includes a stem joined with a lower portion of the substrate, having pins for electrically connecting with the outside, and a hole to pass through external humidity, a wire for electrically connecting the electrode pads of the humidity sensing element and the temperature compensating element with the pins of the stem, and a metal shield case formed on an upper portion of the stem to cover an entire surface of the stem including the humidity sensing element and the temperature compensating element.

18 Claims, 11 Drawing Sheets

ABSOLUTE HUMIDITY SENSOR

This application is the national phase under 35 U.S.C. § 371 of PCT International Application No. PCT/KR00/01439 which has an International filing date of Dec. 12, 2000, which designated the United States of America.

TECHNICAL FIELD

The present invention relates to an absolute humidity sensor, and more particularly, to an absolute humidity sensor for a microwave oven.

BACKGROUND ART

Generally, a humidity sensor is used for various purposes, for example, in a hygrometer, a humidity sensor for cooking of food in a microwave oven, and the like. Examples of currently used humidity sensors include a capacitance type humidity sensor, a relative humidity sensor, and an absolute humidity sensor. The capacitance type humidity sensor is based on variation of dielectric constants by hygroscopic property of an organic material such as polyimide. The relative humidity sensor is based on resistance variation of a semiconductor ceramic, such as $MgCr_2O_4$. The absolute humidity sensor is based on a ceramic thermistor.

Of the humidity sensors, the absolute humidity sensor based on two thermistors is widely used as a humidity sensor for cooking of food in a microwave oven.

The absolute humidity sensor has an advantage in that it can stably detect the humidity because it is not susceptible to variation of a peripheral temperature.

The principles of humidity sensing of the absolute humidity sensor in the microwave oven are based on resistance variation by temperature variation of a thermistor as water vapor generated from food during cooking of food absorbs heat of the thermistor.

FIG. 1 shows a structure of a background art absolute humidity sensor. Referring to FIG. 1, two ceramic thermistors 1 and 2 coated with a passivation film such as a glass film are floating by being connected to a support pin 4 by a precious metal conductor 3, such as platinum. The ceramic thermistors 1 and 2 are packaged by a metal shield case 5 that isolates the two thermistors 1 and 2 from each other.

The thermistor 1 is exposed to the air to allow water vapor to be in contact with a surface of the thermistor 1 by means of a fine hole in the metal shield case 5. The thermistor 1 is used as a sensing element. The other thermistor 2 is sealed in a dry $N_2$ atmosphere by the metal shield case 5 so as not to be in contact with the water vapor. The thermistor 2 is used as a reference element.

Therefore, if a bridge circuit consists of the two thermistors 1 and 2 and an external resistor, the water vapor generated from food during cooking of food absorbs heat of the thermistor 1 exposed to the air. Thus, resistance variation occurs in only the exposed thermistor 1. In this case, output variation occurs due to a bias voltage, thereby detecting the humidity.

Since the background art humidity sensor uses an element as a ceramic thermistor, heat capacity is great, and thus, sensitivity is low. Also, response time is slow and the size of the sensor becomes greater.

Furthermore, the thermistor element is floating using the conductor 3 and the support pin 4 as shown in FIG. 1, and the conductor 3 and the pin 4 are spot-welded. For assembly, the reference element 2 should be sealed in a dry $N_2$. For this reason, the fabrication process steps are complicated and the number of the process steps increases. Also, the cost is expensive and mass production is disadvantageous.

DISCLOSURE OF THE INVENTION

Accordingly, the present invention is directed to an absolute humidity sensor that substantially obviates one or more of the problems due to limitations and disadvantages of the background art.

An object of the present invention is to provide an absolute humidity sensor having an improved sensitivity and high response time.

Another object of the present invention is to provide an absolute humidity sensor having a compact size and simple process steps to facilitate mass production.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, an absolute humidity sensor according to the present invention includes a substrate having a cavity, a membrane formed on the substrate, a resistor formed on the membrane, electrode pads formed on the membrane, for electrically connecting with the resistor, and a passivation film formed on an entire surface of the resistor to cover the resistor.

The membrane is formed of any one of $SiO_2$, $Si_3N_4$, $SiO_xN_y$, and $SiO_2/Si_3N_4/SiO_2$. The resistor is formed of one or more of Ti, Pt, Ni, Ni—Cr, and $VO_2$. The passivation film is formed of any one of $SiO_2$, $Si_3N_4$, $SiO_xN_y$, phosphor silicate glass (PSG), and polyimide.

A thermal conductive film may further be formed on a region of the passivation film where the resistor is formed. At this time, the thermal conductive film is formed of any one of Al and Au.

In another aspect, an absolute humidity sensor according to the present invention includes a substrate having a first cavity and a second cavity in a predetermined region, a membrane formed on the substrate, a humidity sensing element formed on the membrane where the first cavity is formed, for detecting humidity exposed to the air, having a variable resistance value depending on the detected humidity, and a temperature compensating element formed on the membrane where the second cavity is formed, for compensating for the resistance value of the humidity sensing element.

The humidity sensing element and the temperature compensating element include a resistor formed on the membrane, electrode pads formed on the membrane, for electrically connecting with the resistor, and a passivation film formed on an entire surface of the resistor to cover the resistor.

A thermal conductive film may further be formed on a region of the passivation film where the resistor is formed. At this time, the thermal conductive film is formed any one of Al and Au.

A cap may further be formed over the humidity sensing element and the temperature compensating element to cover the entire surfaces of the humidity sensing element and the temperature compensating element, and separates the humidity sensing element and the temperature compensating element from each other and seals them. A shielding film is formed in a central region of the cap to separate and seal the humidity sensing element and the temperature compensating element. A hole is formed in the cap, where the humidity sensing element is formed, to pass through external humidity. The cap is made of silicon.

The absolute humidity sensor according to the present invention further includes a stem joined with a lower portion of the substrate, having pins for electrically connecting with the outside, a wire for electrically connecting the electrode pads of the humidity sensing element and the temperature compensating element with the pins of the stem, and a metal shield case formed on an upper portion of the stem to cover an entire surface of the stem including the humidity sensing element and the temperature compensating element.

A hole is formed in a region of the stem, where the humidity sensing element is formed, or the metal shield case to pass through external humidity.

In the preferred embodiment of the present invention, an absolute humidity sensor having an improved sensitivity to humidity is fabricated using the resistor, and at the same time the sensor is integrated in one chip using a silicon micro-machining process to facilitate its mass production.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

BEST MODE FOR CARRYING OUT THE INVENTION

Reference will now be made in detail to the preferred embodiments of the present invention, examples of which are illustrated in the accompanying drawings.

First Embodiment

Figure 1:
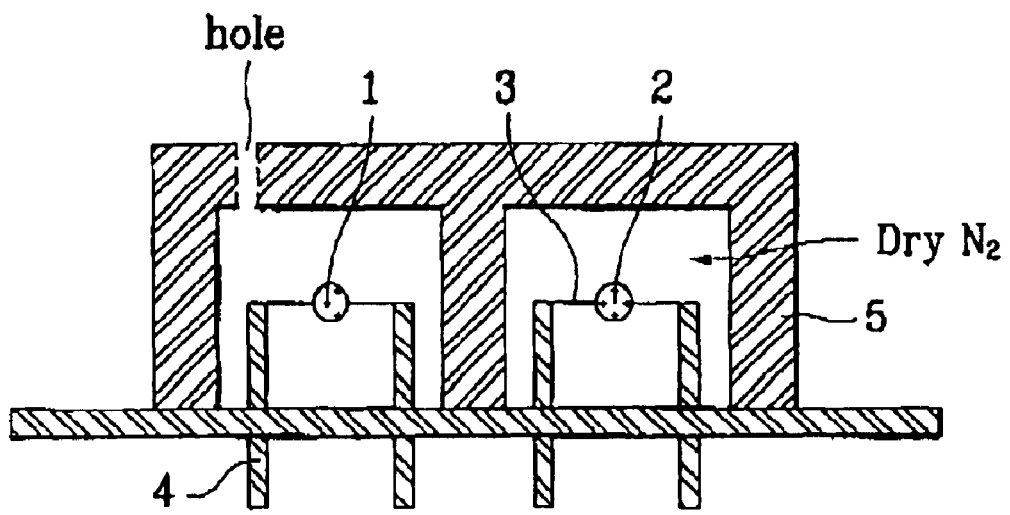
FIG. 1 is a structural sectional view showing a background art of an absolute sensor.
Figure 2:
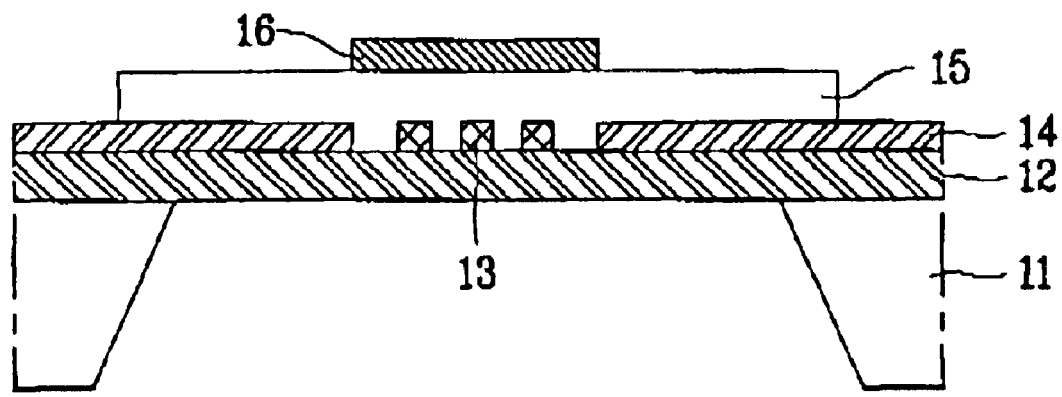
FIG. 2 is a structural sectional view showing a membrane type absolute humidity sensor according to the first embodiment of the present invention.

FIG. 2 is a structural sectional view showing a membrane type absolute humidity sensor according to the first embodiment of the present invention.

As shown in FIG. 2, a membrane 12 of $SiO_2$, $Si_3N_4$, $SiO_xN_y$, or $SiO_2/Si_3N_4/SiO_2$ is formed on a silicon substrate 11. A resistor material having a temperature coefficient of resistance (TCR) is deposited on the membrane 12 and then patterned to form a resistor 13. The resistor is formed of one or more of Ti, Pt, Ni, Ni—Cr, and $VO_2$.

Subsequently, a metal film is deposited on the resistor 13 having the TCR and then patterned to form an electrode pad 14 to be in contact with the resistor 13.

A passivation film 15 is formed on the resistor 13 to cover the resistor 13.

At this time, the passivation film 15 is formed of a material having excellent insulating characteristics, such as $SiO_2$, $Si_3N_4$, $SiO_xN_y$, a PSG, and polyimide.

Next, a metal film such as Al or Au is deposited on the passivation film 15 and then patterned to form a thermal conductive film 16 to be aligned with the resistor 13.

The thermal conductive film 16 acts to quickly emit heat from the resistor 13 to the outside. The thermal conductive film 16 may not be formed as the case may be.

Finally, a rear side of the substrate 11 is etched to expose a region of the membrane 12 where the resistor 13 is formed.

The membrane type absolute humidity sensor fabricated as above requires a temperature compensating element, which is not susceptible to variation of a peripheral humidity, and a humidity sensing element which detects variation of a peripheral humidity.

Figure 3:
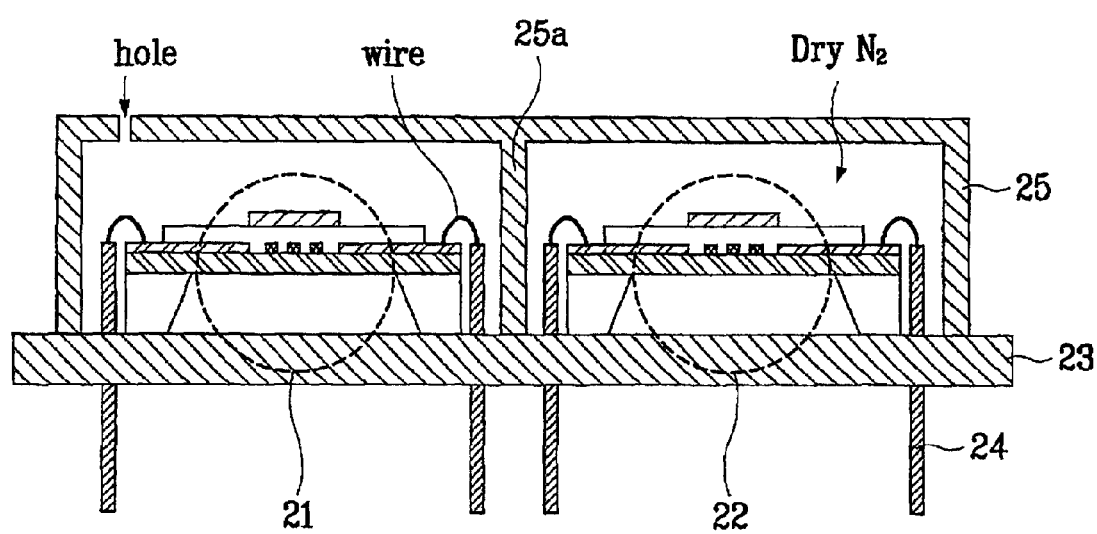
FIG. 3 is a structural sectional view showing a package of the membrane-type absolute humidity sensor according to the first embodiment of the present invention.

FIG. 3 is a structural sectional view showing a package of the membrane type absolute humidity sensor according to the first embodiment of the present invention.

As shown in FIG. 3, an absolute humidity sensor 21 for a humidity sensing element and an absolute humidity sensor 22 for a temperature compensating element are joined on a stem 23. Pins 24 are formed on the stem 23 to electrically connect with the outside. Electrode pads are formed in the absolute humidity sensors 21 and 22. The pins 24 are respectively connected with the electrode pads by wire.

Subsequently, a metal shield case 25 is sealed and joined over the stem to cover an entire surface of the stem 23 including the absolute humidity sensors 21 and 22.

A shielding film 25a is formed in a central region of the metal shield case 25 to separate and seal the absolute humidity sensor 21 for the humidity sensing element and the absolute humidity sensor 22 for the temperature compensating element.

A hole is formed in a region of the metal shield case 25, where the absolute humidity sensor 21 for the humidity sensing element is formed, to pass through external humidity. A dry $N_2$ gas is filled in a region of the metal shield case 25, where the absolute humidity sensor 22 for the temperature compensating element is formed, so as not to be affected by the external humidity.

Second Embodiment

In the second embodiment of the present invention, it is intended that an absolute humidity sensor for a humidity sensing element and an absolute humidity sensor for a temperature compensating element are integrated on one chip to facilitate mass production.

Figure 4:
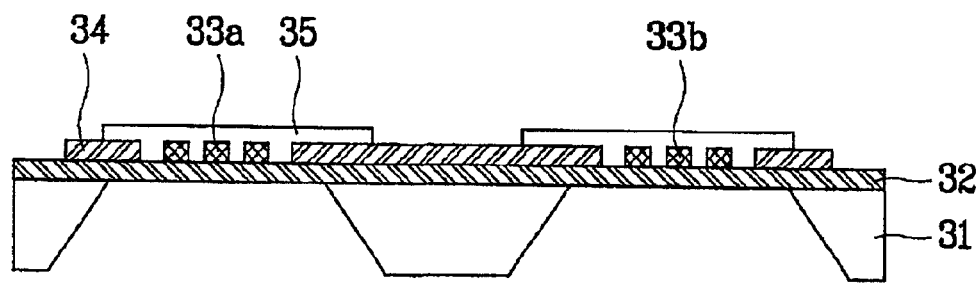
FIG. 4 is a structural sectional view showing a membrane type absolute humidity sensor according to the second embodiment of the present invention.

FIG. 4 is a structural sectional view showing a membrane type absolute humidity sensor according to the second embodiment of the present invention.

As shown in FIG. 4, a membrane 32 of $SiO_2$, $Si_3N_4$, $SiO_xN_y$, or $SiO_2/Si_3N_4/SiO_2$ is formed on a silicon substrate 31. A resistor material having a TCR is deposited on the membrane 32 and then patterned to form a resistor 33 for a humidity sensing element and a resistor 33b for a temperature compensating element. The resistors 33a and 33b are formed of one or more Ti, Pt, Ni, •Ni—Cr, and $VO_2$.

Subsequently, a metal film is deposited on the resistors 33a and 33b having the TCR and then patterned to form an electrode pad 34 to be in contact with the resistors 33a and 33b.

A passivation film 35 is formed on the resistors 33a and 33b to cover entire surfaces of the resistors 33a and 33b.

At this time, the passivation film 35 is formed of a material having excellent insulating characteristics, such as $SiO_2$, $Si_3N_4$, $SiO_xN_y$, a PSG, and polyimide.

Also, a thermal conductive film of Al or Au may be formed on the passivation film 35, to be aligned with the resistors 33a and 33b, as the case may be.

Finally, a rear side of the substrate 31 is etched to expose a region of the membrane 32 where the resistors 33a and 33b are formed.

In the membrane type absolute humidity sensor fabricated as above, a temperature compensating element, which is not susceptible to variation of a peripheral humidity, and a humidity sensing element which detects variation of the peripheral humidity are simultaneously formed on one substrate. Accordingly, it is useful for mass production.

Figure 5:
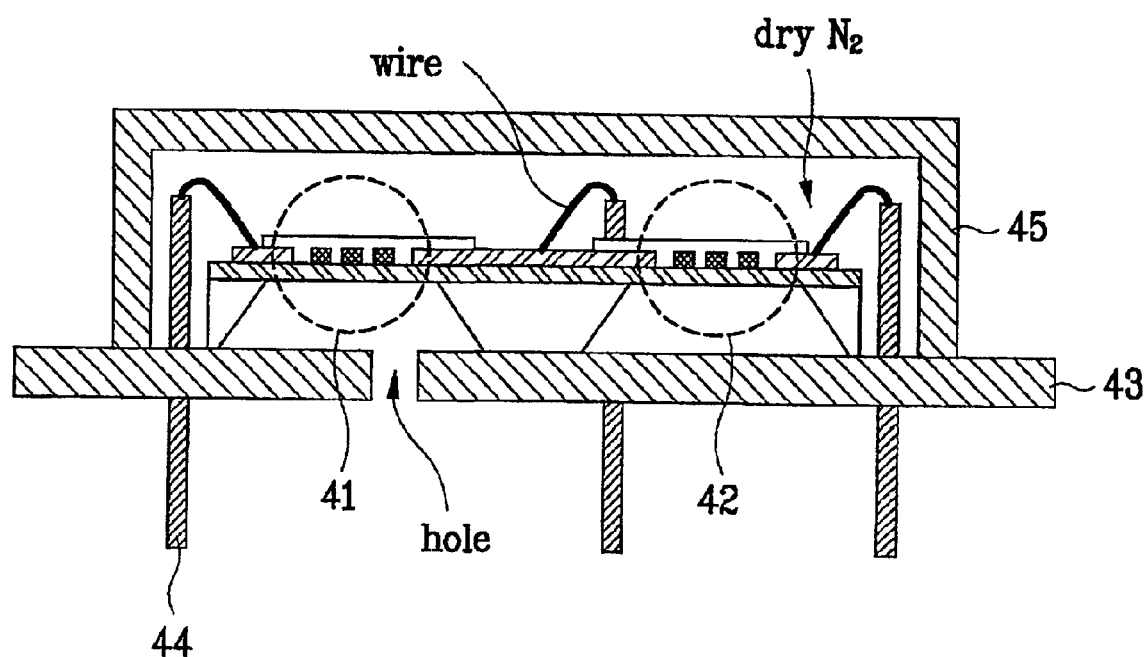
FIG. 5 is a structural sectional view showing a package of the membrane type absolute humidity sensor according to the second embodiment of the present invention.
Figure 6A:
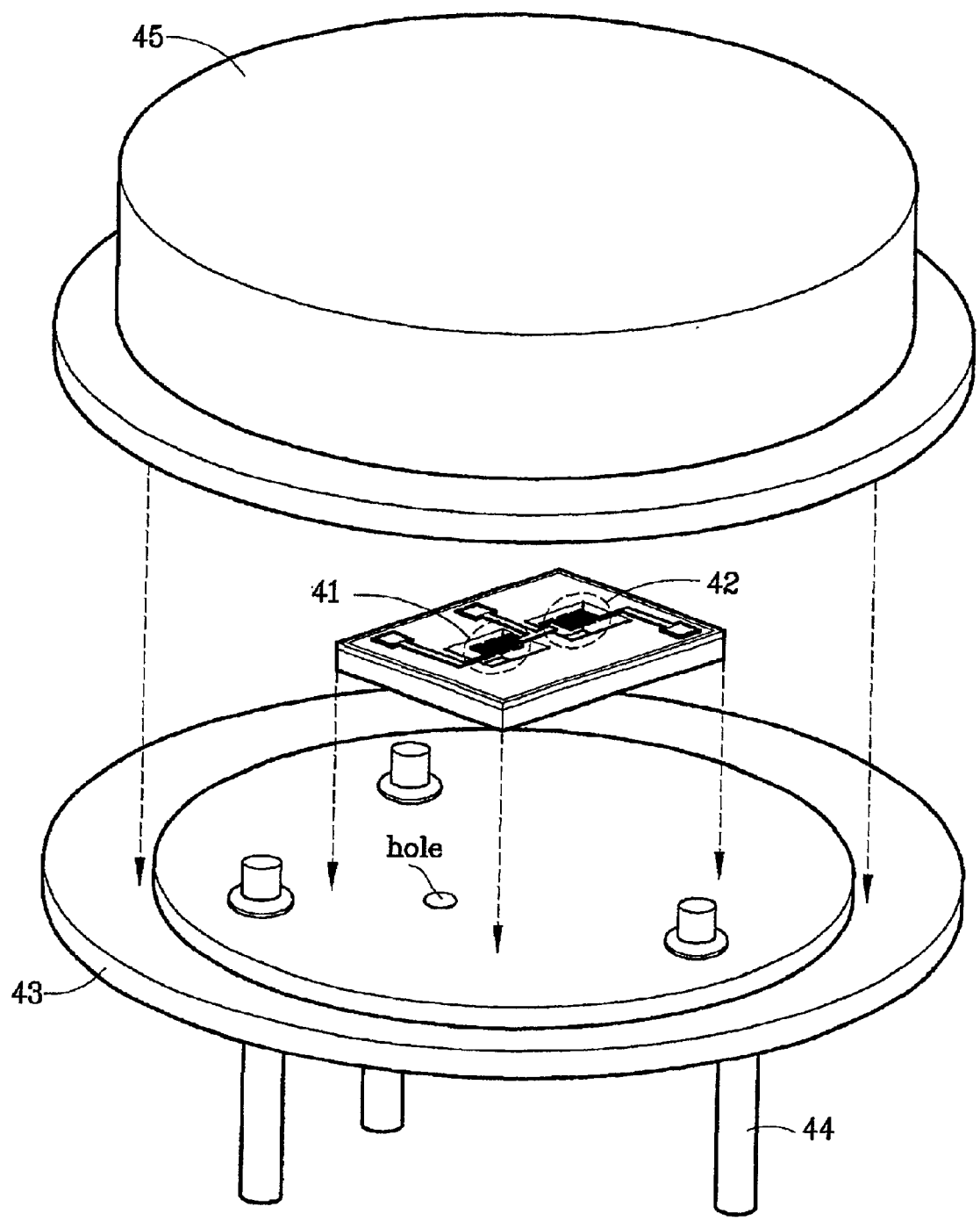
FIGS. 6A and 6B are structural perspective views showing the package of the membrane type absolute humidity sensor according to the second embodiment of the present invention.
Figure 6B:
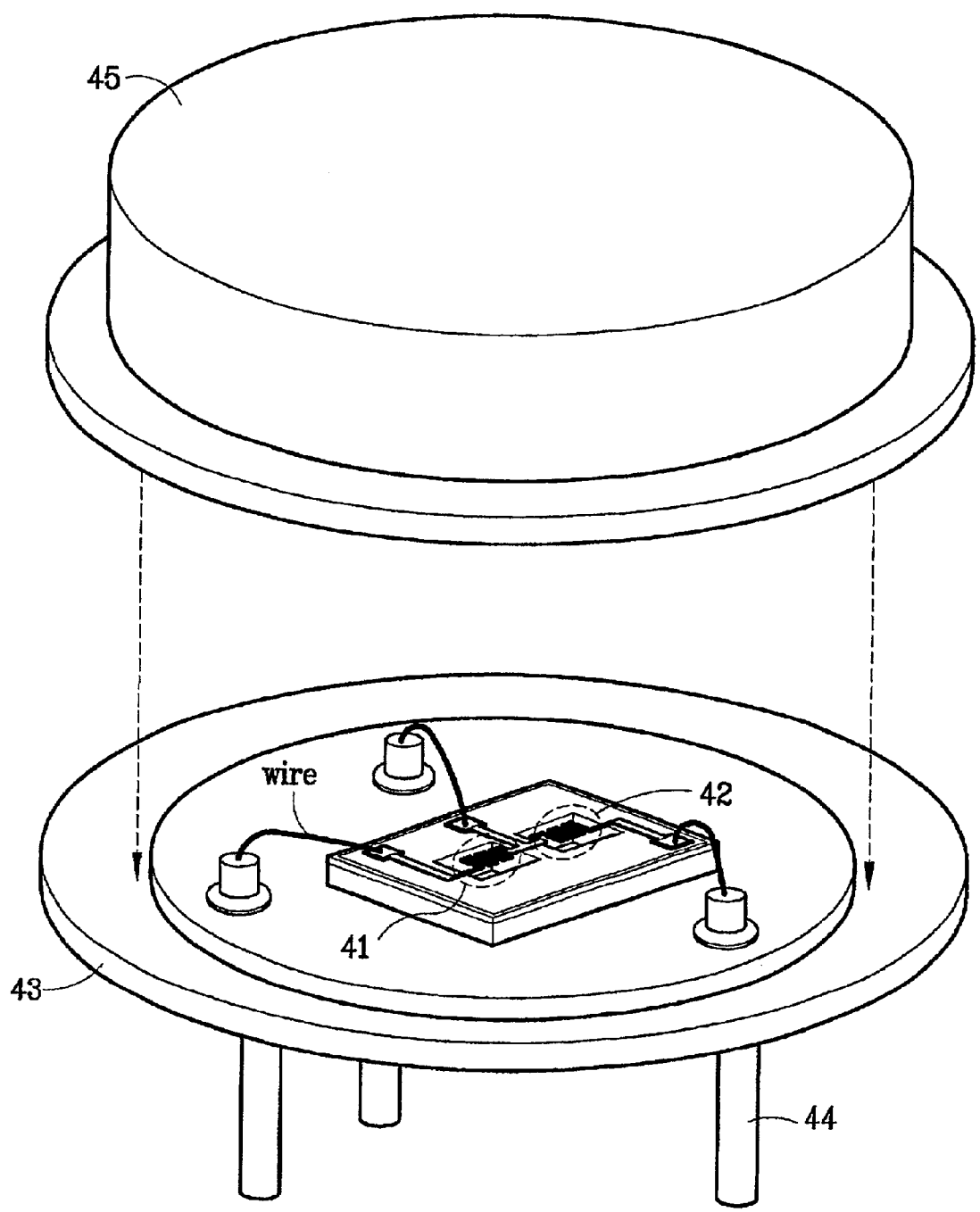

FIG. 5 is a structural sectional view showing a package of the membrane type absolute humidity sensor according to the second embodiment of the present invention, and FIGS. 6A and 6B are structural perspective views showing the package of the membrane type absolute humidity sensor according to the second embodiment of the present invention.

As shown in FIGS. 5, 6A and 6B an absolute humidity sensor provided with a humidity sensing element 41 and a temperature compensating element 42 is joined on a stem 43. Pins 44 are formed on the stem 43 to electrically connect with the outside. Electrode pads are formed in the humidity sensing element 41 and the temperature compensating element 42. The pins 44 are respectively connected with the electrode pads by wire.

Subsequently, a metal shield case 45 is sealed and joined over the stem 43 to cover an entire surface of the stem 43 including the humidity sensing element 41 and the temperature compensating element 42.

Unlike the first embodiment, a shielding film is not formed in the metal shield case 45. A dry $N_2$ gas is filled in upper portions of the humidity sensing element 41 and the temperature compensating element 42 so as not to be affected by the external humidity.

A hole is formed in only a region of the stem 43, where the humidity sensing element is formed, to pass external humidity through the membrane. A region, where the temperature compensating element 42 is formed, is sealed with the substrate 31 so as not to be affected by the external humidity.

Third Embodiment

The third embodiment of the present invention is identical to the second embodiment in its structure.

However, in the third embodiment of the present invention, external humidity is propagated into not a membrane through a stem formed at a lower portion but an insulating film through a shield case and a silicon cap which are formed at an upper portion.

Figure 7:
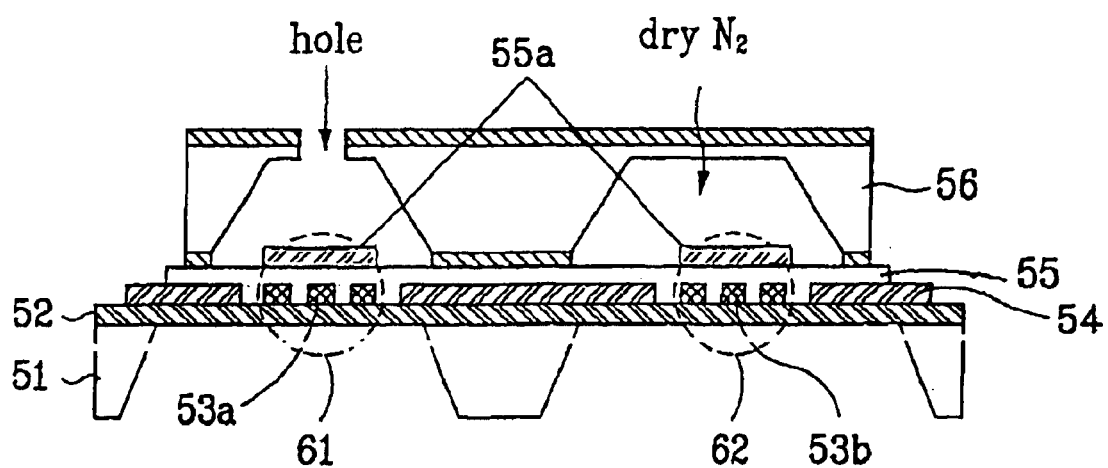
FIG. 7 is a structural sectional view showing a membrane type absolute humidity sensor according to the third embodiment of the present invention.
Figure 8A:
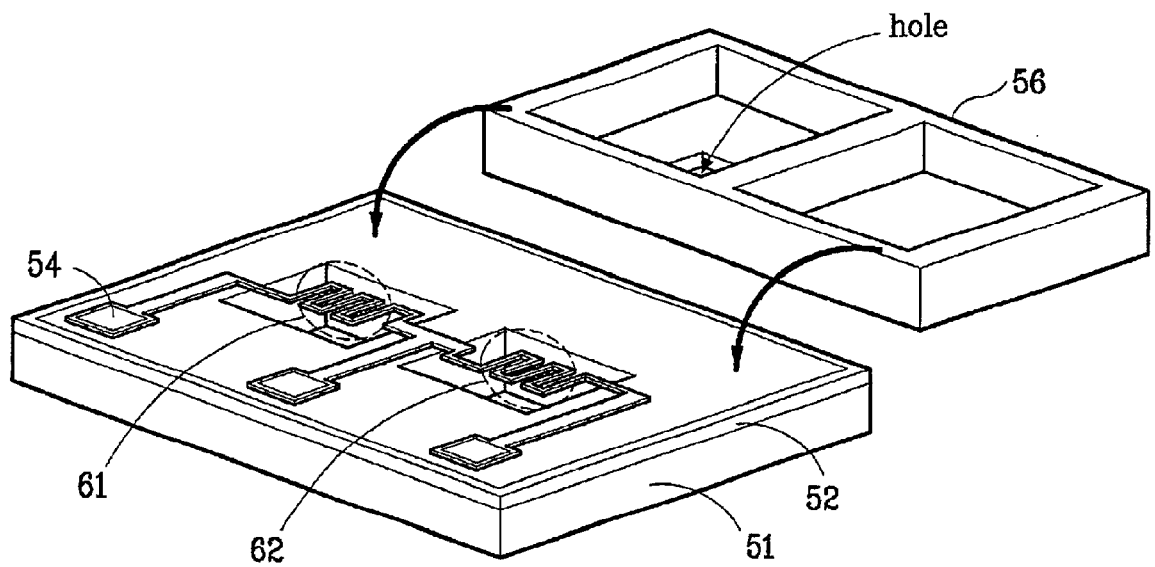
FIGS. 8A and 8B are structural perspective views showing the membrane type absolute humidity sensor according to the third embodiment of the present invention.
Figure 8B:
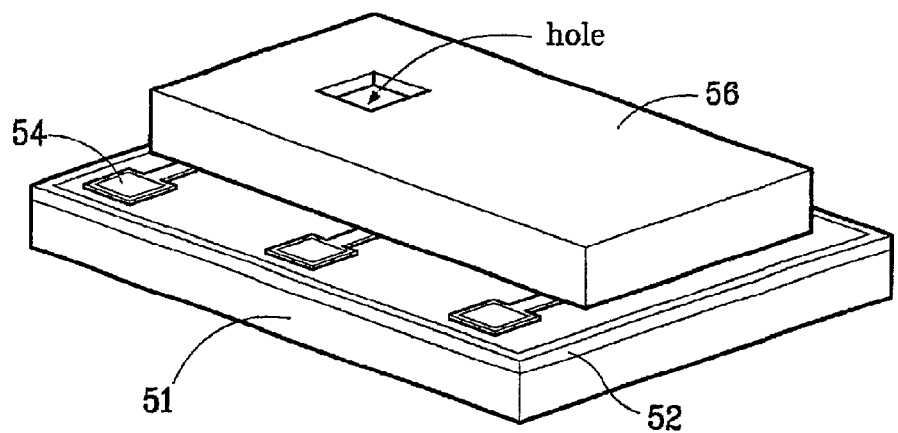

FIG. 7 is a structural sectional view showing a membrane type absolute humidity sensor according to the third embodiment of the present invention, and FIGS. 8A and 8B are structural perspective views showing the membrane type absolute humidity sensor according to the third embodiment of the present invention.

As shown in FIGS. 7, 8A and 8B, a membrane 52 is formed on the silicon substrate 51. A resistor 53a for the humidity sensing element and a resistor 53b for a temperature compensating element are formed on the membrane 52. The resistors 53a and 53b are formed of one or more of Ti, Pt, Ni, Ni—Cr, and $VO_2$.

Subsequently, an electrode pad 54 is formed to be in contact with the resistors 53a and 53b. A passivation film 55 is formed on the resistors 53a and 53b to cover entire surfaces of the resistors 53a and 53b.

At this time, to quickly emit heat the resistors 53a and 53b, as the case may be, a thermal conductive film 55a of Al or Au may be formed on the passivation film 55, to be aligned with the resistors 53a and 53b.

A rear side of the substrate 51 is etched to expose a region of the membrane 52 where the resistors 53a and 53b are formed.

Finally, a silicon cap 56 is sealed and joined in an upper portion of the passivation film 55 to cover entire surfaces of a humidity sensing element 61 and the temperature compensating element 62.

A shielding film is formed in a central region of the silicon cap 56 to separate and seal the humidity sensing element 61 and the temperature compensating element 62.

A hole is formed in a region of the silicon cap 56, where the humidity sensing element 61 is formed, to pass through external humidity. A dry $N_2$ gas is filled in a region of the silicon cap 56, where the temperature compensating element 62 is formed, so as not to be affected by the external humidity.

In the membrane type absolute humidity sensor fabricated as above, the silicon cap covers the humidity sensing element and the temperature compensating element so that the external humidity is upwardly propagated.

The silicon cap according to the third embodiment of the present invention can be fabricated by simple process steps.

Figure 9A:
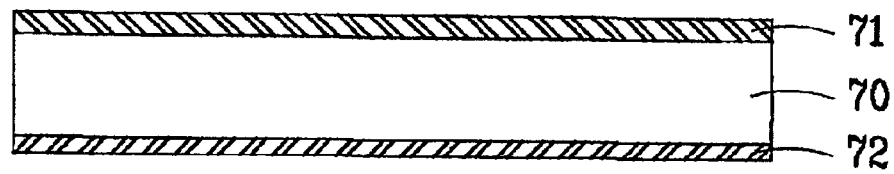
FIGS. 9A through 9C are sectional views showing process steps of fabricating a silicon cap of the membrane type absolute humidity sensor according to the third embodiment of the present invention.
Figure 9B:
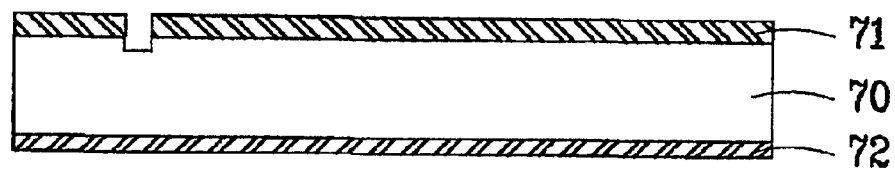
Figure 9C:
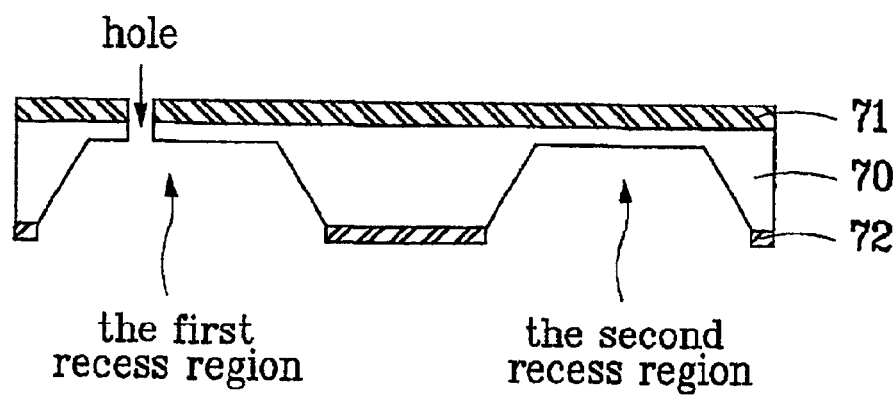

FIGS. 9A through 9C are sectional views showing process steps of fabricating the silicon cap of the membrane type absolute humidity sensor according to the third embodiment of the present invention.

As shown in FIG. 9A, first and second etching mask films 71 and 72 are formed at both sides of a silicon substrate 70. The first and second etching mask films 71 and 72 are formed of $Si_3N_4$ or CrN.

Subsequently, as shown in FIG. 9B, a predetermined region of the first etching mask 71 is removed to expose the silicon substrate 70. The exposed silicon substrate 70 is then etched at a predetermined depth by a wet or dry etching method.

As shown in FIG. 9C, a predetermined region of the second etching mask 72 is removed to expose the silicon substrate 70. The exposed silicon substrate 70 is then etched by the wet or dry etching method to form first and second recess regions. At this time, the silicon substrate 70 is etched at a depth joined with a lower portion of the silicon substrate etched in the step of FIG. 9B.

In the silicon cap of the present invention fabricated as above, the first and second recesses separated from each other by the silicon etching are formed, a hole is formed in a bottom of the first recess to pass through external humidity, and no hole is formed in a bottom of the second recess so as not to pass through the external humidity.

Figure 10A:
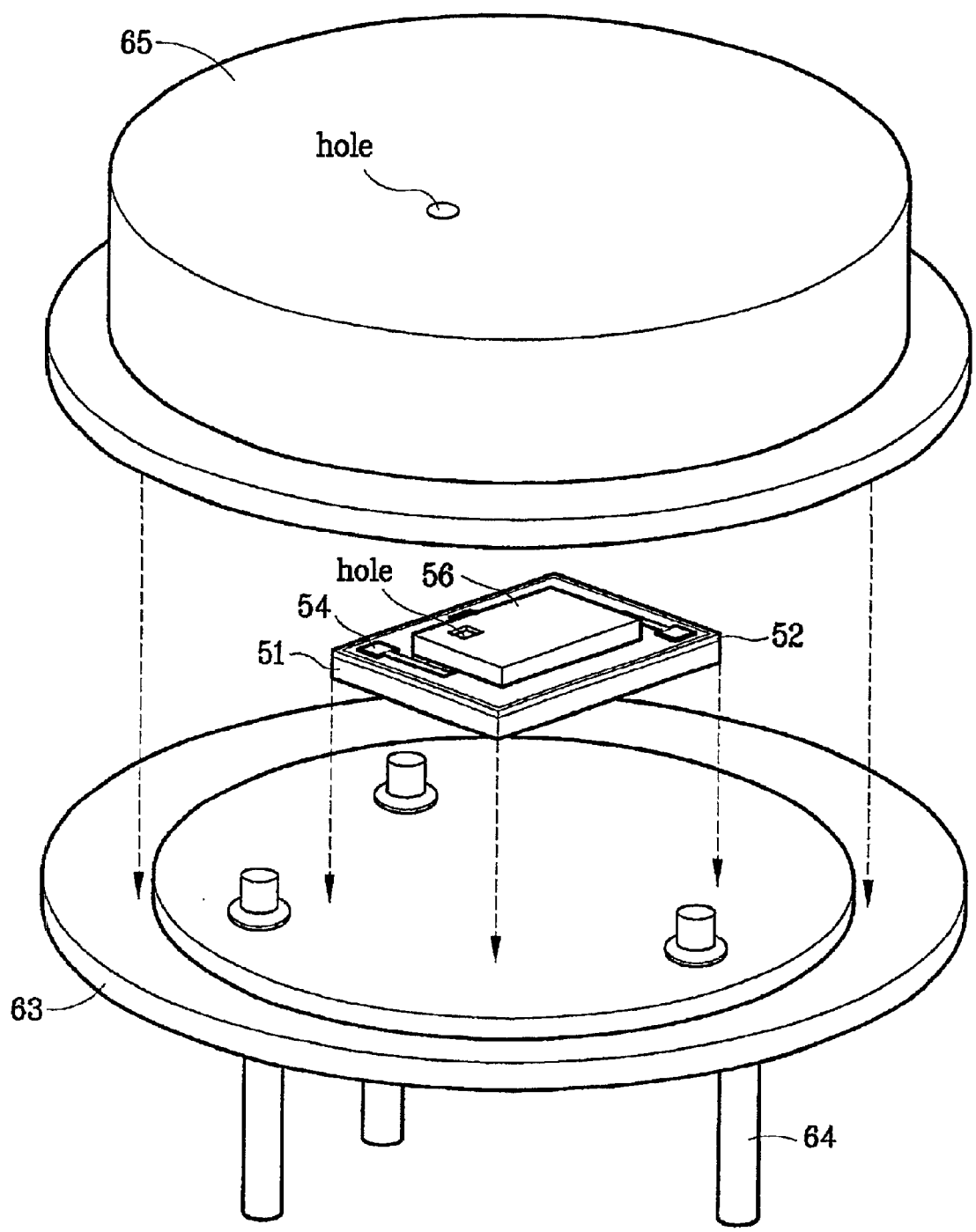
FIGS. 10A and 10B are structural perspective views showing a package of the membrane type absolute humidity sensor according to the third embodiment of the present invention.
Figure 10B:
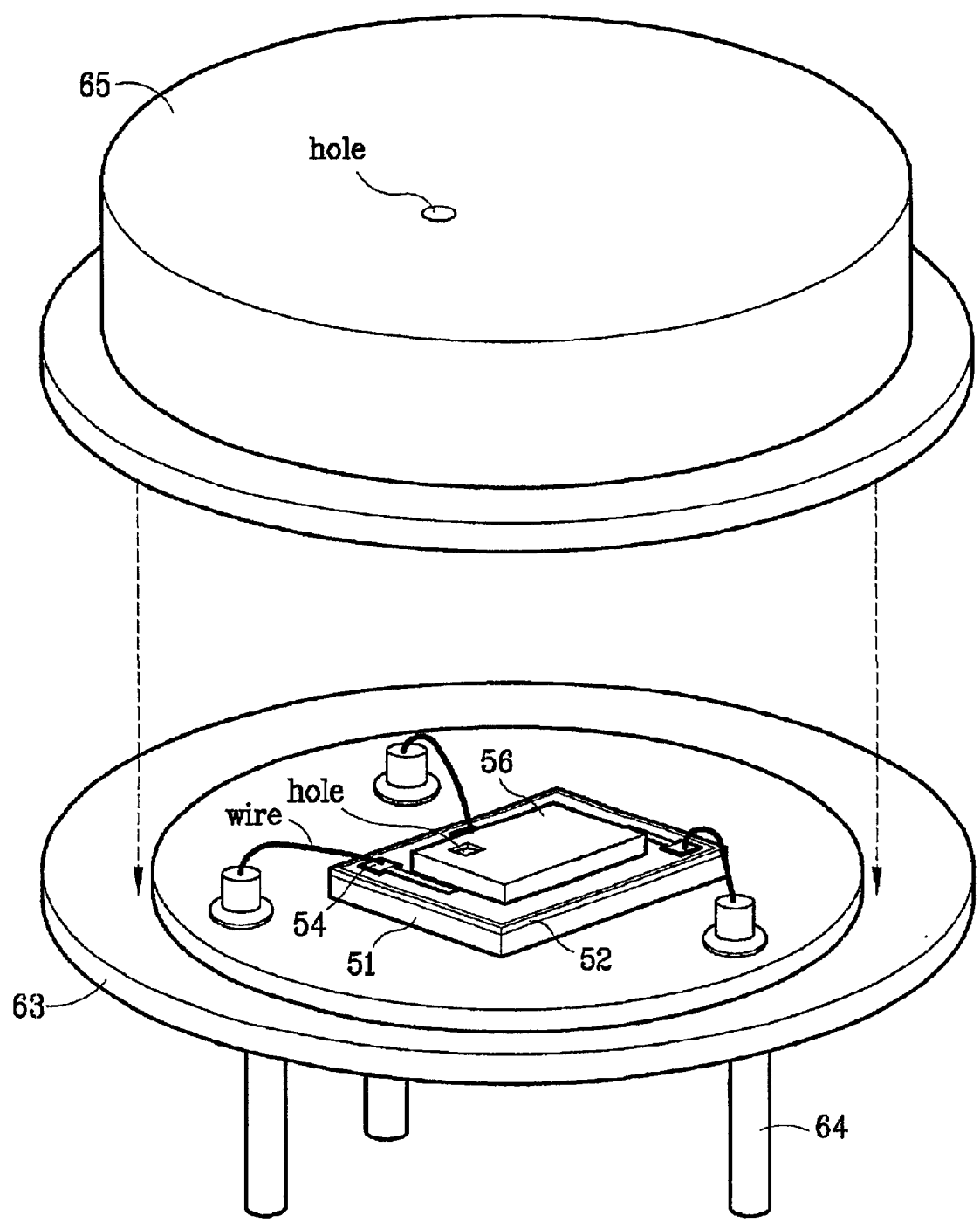

FIGS. 10A and 10B are structure perspective views showing a package of the membrane type absolute humidity sensor according to the third embodiment of the present invention.

As shown in FIGS. 10A and 10B, an absolute humidity sensor provided with a humidity sensing element 61 and the temperature compensating element 62 is joined on a stem 63. Pins 64 are formed on the stem 63 to electrically connect with the outside. Electrode pads are formed in the humidity sensing element 61 and the temperature compensating element 62. The pins 64 are respectively connected with the electrode pads by wire.

Subsequently, a metal shield case 65 is sealed and joined over the stem 63 to cover an entire surface of the stem 63 including the silicon cap 56.

Unlike the first embodiment, a shielding film is not formed in the metal shield case 65. A hole is formed in the metal shield case 65 to pass through the external humidity. That is, the external humidity is propagated into a region, where the humidity sensing element 61 is formed, through the hole of the metal shields case 65 and the hole of the silicon cap 56.

Figure 11:
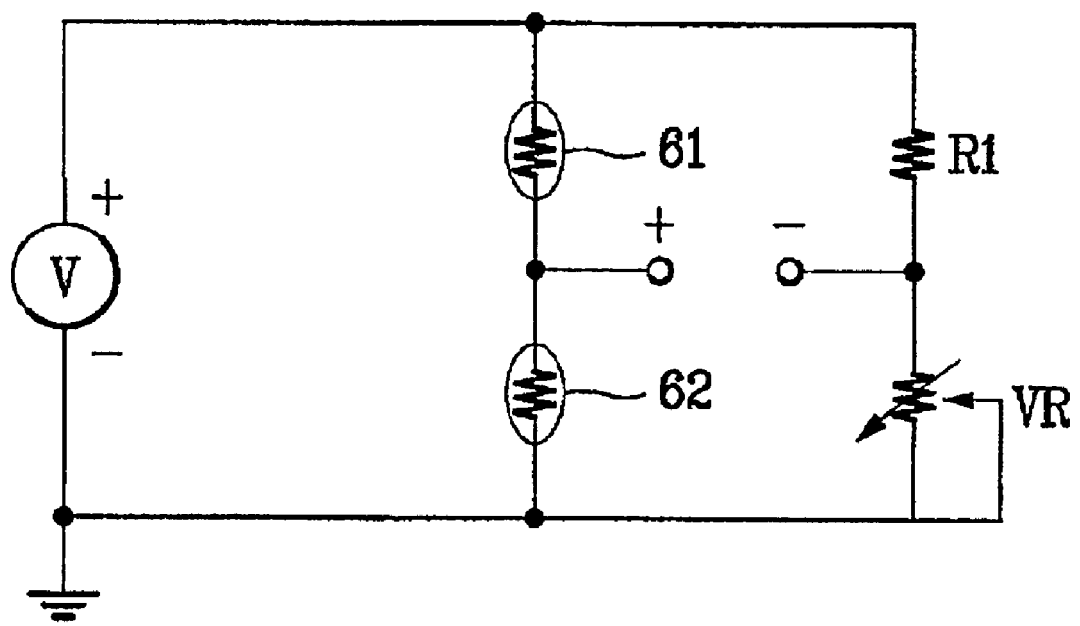
FIG. 11 is a circuit diagram for detecting humidity based on the membrane type absolute humidity sensor according to the present invention.

FIG. 11 is a circuit diagram for detecting the humidity based on the membrane type absolute humidity sensor according to the present invention.

Referring to FIG. 11, the circuit for detecting variation of the peripheral humidity using the membrane type absolute humidity sensor according to the present invention includes a bridge circuit and a power source (V) applied to the bridge circuit. The bridge circuit consists of a humidity sensing element 61, a temperature compensating element 62, a fixed resistor R1, and a variable resistor VR.

As an example, a method for detecting variation of the humidity by water vapor generated from food during cooking of food in a microwave oven using the absolute humidity sensor and the above circuit will be described below.

First, if the food is heated in the microwave oven, the water vapor is generated. The generated water vapor is propagated into the sensor through a hole formed inside the sensor. Thus, the water vapor is in contact with the humidity sensing element 61.

At this time, a resistor of the humidity sensing element 61 is self-heated by a bias voltage. Accordingly, the water vapor contacted with the humidity sensing element 61 absorbs heat of the resistor. For this reason, the resistor from the humidity sensing element 61 has a reduced temperature by heat loss, thereby varying a resistance value.

However, since the temperature compensating element 62 does not contact the water vapor, variation of a resistance value does not occur.

The resistance variation of the humidity sensing element 61 causes an output variation of the bridge circuit, thereby detecting the humidity variation.

Accordingly, the humidity variation around the sensor can easily be detected by the absolute humidity sensor and the above circuit. The water vapor generated from the food due to heat during cooking of food in a cooking machine, such as a microwave oven, is detected to apply for automatic cooking of food.

Industrial Applicability

As aforementioned, the membrane type absolute humidity sensor according to the present invention has the following advantages.

Since the resistor having the TCR is formed, it is possible to improve sensitivity of the sensor and obtain high response time. Furthermore, since the sensor is integrated in one chip using a silicon micro-machining process, a compact size and simple process steps can be achieved to facilitate mass production. Also, the production cost can be saved.

The foregoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. An absolute humidity sensor comprising:
    a substrate having a cavity;
    a membrane formed on the substrate;
    a resistor formed on the membrane;
    electrode pads formed on the membrane, for electrically connecting with the resistor;
    a passivation film formed on an entire surface of the resistor to cover the resistor; and
    a thermal conductive film formed on a region of the passivation film where the resistor is formed.

2. The absolute humidity sensor of claim 1, wherein the membrane is formed of any one of $SiO_2$, $Si_3N_4$, $SiO_xN_y$, and $SiO_2/Si_3N_4/SiO_2$.

3. The absolute humidity sensor of claim 1, wherein the resistor is formed of one or more of Ti, Pt, Ni, Ni—Cr, and $VO_2$.

4. The absolute humidity sensor of claim 1, wherein the passivation film is formed of any one of $SiO_2$, $Si_3N_4$, $SiO_xN_y$, phosphor silicate glass (PSG), and polyimide.

5. The absolute humidity sensor of claim 1, wherein the thermal conductive film is formed of any one of Al and Au.

6. An absolute humidity sensor comprising:
    A substrate having a first cavity and a second cavity in a predetermined region;
    a membrane formed on the substrate;
    a humidity sensing element formed on the membrane where the first cavity is formed, for detecting humidity exposed to the air, having a variable resistance value depending on the detected humidity;
    a temperature compensating element formed on the membrane where the second cavity is formed, for compensating for the resistance value of the humidity sensing element, and
    a thermal conductive film formed on a region of passivation film where a resistor is formed.

7. The absolute humidity sensor of claim 6, wherein the humidity sensing element and the temperature compensating element include:

said resistor formed on the membrane;

electrode pads formed on the membrane, for electrically connecting with the resistor; and said passivation film formed on an entire surface of the resistor to cover the resistor.

8. The absolute humidity sensor of claim 7, wherein the membrane is formed of any one of $SiO_2$, $Si_3N_4$, $SiO_xN_y$, and $SiO_2/Si_3N_4/SiO_2$.

9. The absolute humidity sensor of claim 7, wherein the resistor is formed of one or more of Ti, Pt, Ni, Ni—Cr, and $VO_2$.

10. The absolute humidity sensor of claim 7, wherein the passivation film is formed of any one of $SiO_2$, $Si_3N_4$, $SiO_xN_y$, phosphor silicate glass (PSG), and polyimide.

11. The absolute humidity sensor of claim 6, wherein the thermal conductive film is formed of any one of Al and Au.

12. The absolute humidity sensor of claim 6, further comprising a cap formed over the humidity sensing element and the temperature compensating element to cover the entire surfaces of the humidity sensing element and the temperature compensating element, for separating the humidity sensing element and the temperature compensating element from each other and sealing them therein.

13. The absolute humidity sensor of claim 12, wherein a shielding film is formed in a central region of the cap to separate and seal the humidity sensing element and the temperature compensating element.

14. The absolute humidity sensor of claim 12, wherein a hole is formed in a region of the cap, where the humidity sensing element is formed, to pass through external humidity.

15. The absolute humidity sensor of claim 12, wherein the cap is made of silicon.

16. The absolute humidity sensor of claim 6, further comprising:

a stem joined with a lower portion of the substrate, having pins for electrically connecting with the outside;

a wire for electrically connecting electrode pads of the humidity sensing element and the temperature compensating element with the pins of the stem; and a metal shield case formed on an upper portion of the stem to cover an entire surface of the stem including the humidity sensing element and the temperature compensating element.

17. The absolute humidity sensor of claim 16, wherein a hole is formed in a region of the stem, where the humidity sensing element is formed, to pass through external humidity.

18. The absolute humidity sensor of claim 16, wherein a hole is formed in the shield case to pass through external humidity.

* * * * *

UNITED STATES PATENT AND TRADEMARK OFFICE
Certificate

Patent No. 6,840,103 B2                                                            Patented: January 11, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Don Hee Lee, Kyonggi-do, Korea; Hyung Ki Hong, Kyonggi-do, Korea; and Geun Ho Kim, Seoul, Korea.

Signed and Sealed this Twenty-second Day of November 2005.

HEZRON E. WILLIAMS
*Supervisory Patent Examiner*
Art Unit 2856